US00PP11236P

United States Patent [19]

Pieters

[11] Patent Number: Plant 11,236

[45] Date of Patent: Feb. 22, 2000

[54] CHRYSANTHEMUM PLANT NAMED 'GEDI RT'

[76] Inventor: Dirk Pieters, Schierveldestraat 3A, Oosnieuwkerke, 8840 Staden, Belgium

[21] Appl. No.: 09/126,003

[22] Filed: Jul. 29, 1998

[51] Int. Cl.[7] ..... A01H 5/00

[52] U.S. Cl. ..... Plt./298

[58] Field of Search ..... Plt./296, 298

*Primary Examiner*—Howard J. Locker

*Attorney, Agent, or Firm*—Christie, Parker & Hale, LLP

[57] ABSTRACT

A new variety of Chrysanthemum producing red daisy-type flowers.

1 Drawing Sheet

BACKGROUND OF THE INVENTION

The present invention is directed to a new and distinct variety of Chrysanthemum botanically classified as *Dendranthema grandiflora*. The varietal denomination of the new Chrysanthemum is 'GEDI RT'.

The new variety was discovered as a natural branch mutation of the variety 'Tripoli' (U.S. Plant Pat. No. 10,207) in Staden, Belgium. The new variety has been asexually reproduced by vegetative cuttings in Ventura County, Calif. and the distinguishing characteristics are retained through successive generations of asexual reproduction.

SUMMARY OF THE INVENTION

'GEDI RT' is pot type Chrysanthemum plant variety that produces red, daisy-type flowers.

COMPARISON WITH PARENT

The new variety differs from its parent in producing red ray florets whereas ray florets of the parent are lavender.

BRIEF DESCRIPTION OF ILLUSTRATION

The accompanying photograph shows a typical specimen of the new variety with colors being as nearly true as possible with illustrations of this type.

DESCRIPTION OF THE PLANT

The following description of the new variety is of specimens grown in a greenhouse in Ventura County, Calif. in the month of April. 'GEDI RT' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about ten days after planting, with center bud removed. It has been observed that the shelf life of 'GEDI RT' is about 20 days with the response time of about 9 weeks. No growth regulator is used with the plants described. Desirable growing conditions include average night temperatures of about 62°–65° F. and day temperatures of about 70°–75° F.

Plant:

*Habit.*—Non-brittle, mounding perennial.

*Height.*—16 cm.

*Number of breaks from pinch.*—6 to 7.

*Length of lateral branches.*—14 cm.

*Stem color.*—138B.

Foliage:

*Leaf arrangement.*—Alternate.

*Number of leaves per lateral branch.*—About 10 fully expanded leaves.

*Leaf size.*—Length: About 4.2 cm. Width: About 2.1 cm.

*Leaf shape.*—Ovate.

*Attachment.*—Petioled.

*Leaf apex.*—Acute.

*Base.*—Tapered.

*Margin.*—Palmately lobed.

*Aspect.*—Slightly undulating.

*Surface.*—Top: Lightly pubescent. Bottom: Lightly pubescent.

*Venation.*—Prominent mid vein on underside. Mid vein: Color underside: Near 144A. Color upperside: Near 144B.

*Petiole.*—Length: About 1.1 cm. Color: Near 137B. Mature leaf: Top: Near 137A. Bottom: Near 138B. Young leaf: Top: Near 137B. Bottom: Near 138B.

Flower:

*Inflorescence form.*—Cyme.

*Flower form.*—Daisy.

*Number of blooms per branch.*—About 10.

*Diameter of fully expanded bloom.*—About 4.5 cm.

*Depth of fully expanded bloom.*—About 1.2 cm

*Diameter of disc.*—About 1.3 cm.

*Sepal number.*—About 35. Color: Near 137B.

*Peduncle.*—Length: About 3.5 cm. Habit: Undulating. Surface: Pubescent. Color: Near 138A.

*Flower bud* (*when just showing color*).—Color: Near 44C. Diameter: About 0.7 cm. Height: About 1 cm. Shape: Obovoid.

*Ray florets.*—Number per flower: About 30. Texture: Matte. Shape: Oblanceolate. Apex: Obtuse. Base: Fused. Margin: Entire. Aspect: Slightly curved. Length: About 2.1 cm. Width: About 0.4 cm

*Disc florets.*—Number per flower: About 100. Texture: Glossy. Shape: Cylindrical. Margin: Entire. Length: About 0.4 cm. Width: About 0.08 cm.

*Fragrance.*—Moderate.

Flower color:

*General flower coloration.*—Red, daisy-type with a yellow/orange disc.

*Ray florets, top side.*—Immature: Near 44C. Mature: Near 46C. Fading: Near 42B.

*Ray floret, under side.*—Immature: Near 42B. Mature: Near 42B. Fading: Near 42C.

*Disc florets.*—Immature: Near 5B. Mature: Near 15B. Fading: Near 15B.

*Changes as the flower ages.*—Daisy form becomes very open and abundant, pollen is released. Flower color fades slightly, more orange/red tones apparent.

Reproductive organs:

*Ray florets.*—Pistillate. Stigma shape: 2 branched. Stigma color: Near 2B Style length: About 0.2 cm. Style color: Near 1D.

*Disc florets.*—Stigma shape: Linear. Stigma color: Near 2B. Style length: About 0.2 cm. Style color: Near 15B. Stamen number: About 5. Anther length: About 0.2 cm. Pollen color: Near 15B. Pollen quantity: Abundant.

What is claimed is:

1. A new and distinct Chrysanthemum plant of the variety substantially as herein shown and described.

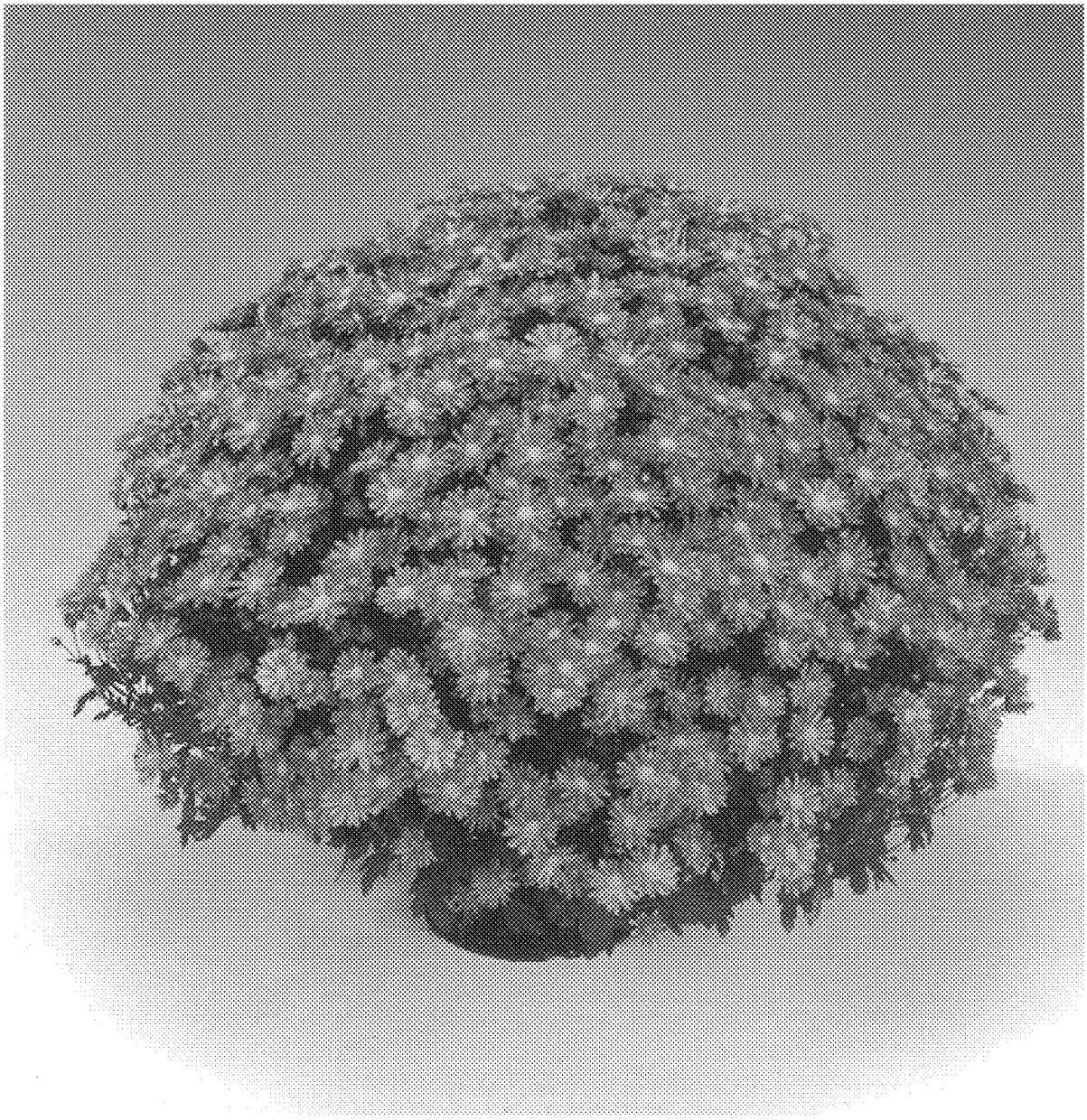

* * * * *